US009005683B2

(12) United States Patent
Shibuya et al.

(10) Patent No.: US 9,005,683 B2
(45) Date of Patent: Apr. 14, 2015

(54) METHOD FOR PRODUCING YEAST WITH HIGH GLUTAMIC ACID CONTENT (75) Inventors: Ichiro Shibuya, Tokyo (JP); Hiroaki Okano, Nagareyama (JP); Yoshitomo Kanaoka, Kashiwa (JP); Nobuchika Takesue, Moriya (JP)

(73) Assignee: Asahi Group Holdings, Ltd. (JP)

( * ) Notice: Subject to any disclaimer, the term of this patent is extended or adjusted under 35 U.S.C. 154(b) by 0 days.

(21) Appl. No.: 13/128,677

(22) PCT Filed: Oct. 30, 2009

(86) PCT No.: PCT/JP2009/005802
§ 371 (c)(1),
(2), (4) Date: May 11, 2011

(87) PCT Pub. No.: WO2010/058527
PCT Pub. Date: May 27, 2010

(65) Prior Publication Data
US 2011/0223287 A1    Sep. 15, 2011

(30) Foreign Application Priority Data

Nov. 18, 2008  (JP) ................................. 2008-294642
May 19, 2009  (WO) ................. PCT/JP2009/059206

(51) Int. Cl.
*A23L 1/28* (2006.01)
*A23C 9/12* (2006.01)
*C12N 1/00* (2006.01)
*C12N 1/16* (2006.01)
*A23L 1/228* (2006.01)
*A23L 1/30* (2006.01)
*A23L 1/305* (2006.01)
*A23L 1/39* (2006.01)
*A23L 2/56* (2006.01)
*C12N 1/18* (2006.01)

(52) U.S. Cl.
CPC . *C12N 1/16* (2013.01); *A23L 1/228* (2013.01); *A23L 1/3018* (2013.01); *A23L 1/3051* (2013.01); *A23L 1/39* (2013.01); *A23L 2/56* (2013.01); *C12N 1/18* (2013.01)

(58) Field of Classification Search
USPC .......................................... 435/106, 108, 116
See application file for complete search history.

(56) References Cited

U.S. PATENT DOCUMENTS

| | | | | |
|---|---|---|---|---|
| 3,616,234 A | * | 10/1971 | Komagata et al. | 435/224 |
| 3,888,839 A | * | 6/1975 | Newell et al. | 530/371 |
| 3,914,450 A | * | 10/1975 | Robbins et al. | 426/533 |
| 4,584,269 A | | 4/1986 | Vollmer et al. | |
| 4,810,509 A | | 3/1989 | Kanegae et al. | |
| 6,344,231 B1 | | 2/2002 | Nakajo et al. | |

FOREIGN PATENT DOCUMENTS

| | | |
|---|---|---|
| AU | 2009232936 A1 | 10/2009 |
| EP | 0 143 560 A2 | 6/1985 |
| EP | 0 805 202 A1 | 11/1997 |
| GB | 1196391 A | 6/1970 |
| JP | B-39-16342 | 8/1964 |
| JP | B-54-31076 | 10/1979 |
| JP | A-60-133892 | 7/1985 |
| JP | 62-275667 | 11/1987 |
| JP | A-63-123390 | 5/1988 |
| JP | 2-219560 | 9/1990 |
| JP | 5-227911 | 9/1993 |
| JP | 9-47295 | 2/1997 |
| JP | 9-276843 | 10/1997 |
| JP | 9-294581 | 11/1997 |
| JP | 9-313169 | 12/1997 |
| JP | 3896606 | 12/1997 |
| JP | 10327802 A * | 12/1998 |
| JP | A-10-327802 | 12/1998 |
| JP | 3088709 | 2/2000 |
| JP | B-3088709 | 7/2000 |
| JP | 2002-171961 | 6/2002 |
| JP | 2002-355008 | 12/2002 |
| JP | 2003-38123 | 2/2003 |
| JP | B-3519572 | 4/2004 |
| JP | 2004-248529 | 9/2004 |
| JP | 2004/254545 | 9/2004 |
| JP | 2004-290183 | 10/2004 |
| JP | 2005-102549 | 4/2005 |

(Continued)

OTHER PUBLICATIONS

Monosodium Glutamate (MSG), Glutamic Acid (Glutamate), Glutamine Review by Dr. Misner, Hammer Nutrition, pp. 1-5 Jul. 11, 2007.*
L-Alanine as an end product of glycolysis in *Saccharomyces cerevisiae* growing under different hypoxic conditions by E.Chico et al., Antonie van Leeuwenhoek, vol. 44, No. 2 (1978).*
Lactate and Amino Acid Catabolism in the Cheese-Ripening Yeast *Yarrowia lipolytica*, by Mansour et al., Applied and Environmental Microbiology, Nov. 2008, p. 6505-6512.*
Microbiology including Immunology and Molecular Genetics by David et al., Haper & Row Publishers 1980, pp. 64-65.*

(Continued)

*Primary Examiner* — Kade Ariani
(74) *Attorney, Agent, or Firm* — Merchant & Gould P.C.

(57) ABSTRACT

Provided is a method for producing a yeast containing glutamic acid at a high concentration. In the method for culturing a yeast, a yeast in a stationary growth phase is subjected to liquid culture under the conditions that the pH of a liquid medium is 7.5 or higher and lower than 11. After the pH of the liquid medium for the yeast in a stationary growth phase is adjusted to 7.5 or higher and lower than 11, the yeast is further cultured, whereby a yeast with a high glutamic acid content can be produced. In the invention, as the yeast, *Saccharomyces cerevisiae* or *Candida utilis* can be used. Therefore, by using the yeast with a high glutamic acid content obtained by the above-said method and the extract obtained by extraction from the yeast, a seasoning composition and a food or drink with a high glutamic acid content can be provided.

6 Claims, 2 Drawing Sheets

(56) References Cited

FOREIGN PATENT DOCUMENTS

| JP | 2006-067813 | 3/2006 |
|---|---|---|
| JP | 2006-129835 | 5/2006 |
| JP | A 2006-280253 | 10/2006 |
| JP | 2007-049989 | 3/2007 |
| WO | WO 98/35049 | 8/1998 |
| WO | WO 98/46089 | 10/1998 |
| WO | WO 2007/015470 A1 | 2/2007 |
| WO | WO 2007/129701 A1 | 11/2007 |
| WO | WO 2009/123019 A9 | 10/2009 |

OTHER PUBLICATIONS

Bogonez et al., Journal of General Microbiology, 1985, vol. 131, p. 1425-1432.*
Aon et al., Antonie van Leeuwenhoek, 1996, vol. 69, p. 257-265.*
Dickenson et al., Eur. J. Biochem., 1985, vol. 148, p. 405-406.*
Australian Office Action for Australian Application No. 2009318734 mailed Jul. 3, 2012.
European Search Report for EP 9827308.9 (mailed Jul. 5, 2012).
US Office Action for U.S. Appl. No. 13/126,514 (mailed Mar. 29, 2012).
US Office Action for U.S. Appl. No. 13/126,514 (mailed Oct. 24, 2012).
US Office Action for U.S. Appl. No. 13/128,683 (mailed Mar. 28, 2012).
US Office Action for U.S. Appl. No. 13/128,683 (mailed Oct. 11, 2012).
International Search Report for International Application No. PCT/JP2009/006165 (mailed Dec. 28, 2009).
International Search Report for International Application No. PCT/JP2009/006148 (mailed Dec. 28, 2009).
European Search Report for European Application No. 09 82 7332 mailed Aug. 8, 2012.
European Search Report for European Application No. 09 82 7339 mailed Aug. 8, 2012.
Japanese Office Action for Japanese Application No. 2010-042776 mailed Oct. 15, 2013.
European Office Action for European Application No. 09827308.9 mailed Oct. 17, 2013.
Bogonez et al. "Ammonia Accumulation in Acetate-Growing Yeast," *Biochemica et Biophysica Acta* 773: 234-271 (1983).
International Search Report for International application No. PCT/JP2009/005802 mailed Nov. 24, 2009 (Form PCT/ISA/210).
International Search Report for International application No. PCT/JP2009/059206 mailed Jun. 16, 2009 (Form PCT/ISA/210).
Office Action for JP Application No. 2009-554805 mailed Sep. 7, 2010.
Decision of Rejection for JP Application No. 2009-554805 mailed Dec. 14, 2010.
Office Action for U.S. Appl. No. 13/126,514 mailed Dec. 2, 2014.
Office Action for U.S. Appl. No. 13/128,683 mailed Dec. 5, 2014.
Fay et al., "Evidence for Domesticated and Wild Populations of *Saccharomyces cerevisiae*," *PLOS Genetics*, 1(1):66-71 (2005).

* cited by examiner

METHOD FOR PRODUCING YEAST WITH HIGH GLUTAMIC ACID CONTENT

This application is a National Stage Application of PCT/JP2009/005802, filed 30 Oct. 2009, which claims the benefit of Japanese Patent Application No. 2008-294642, filed 18 Nov. 2008 in Japan and International Application No. PCT/JP2009/059206, filed 19 May 2009 in the International Bureau, the disclosures of all of which are hereby incorporated by reference in their entireties. To the extent appropriate, a claim of priority is made to each of the above disclosed applications. The International Application was published in Japanese on 27 May 2010 as WO 20101058527.

TECHNICAL FIELD

The present invention relates to a method for producing a yeast with a high glutamic acid content, a yeast with a high glutamic acid content, a yeast extract with a high glutamic acid content, and a food or drink containing a yeast extract with a high glutamic acid content.

BACKGROUND ART

There is currently a worldwide demand for a natural and health-oriented non-artificial seasoning with no use of additives, as led by Japan and developed countries including European countries and the U.S. Regarding this demand, although a high-value added extract with enhanced "umami" such as nucleic acid has been developed in the yeast extract industry, development is also progressing for amino acids, such as glutamic acid, which is a representative of "umami" equivalent to nucleic acid.

Glutamic acid has been in widespread use for a long time in the form of sodium glutamate as a chemical seasoning or the like. Recently, preference has been shown for the utilization of a culture or extract or the like, which is obtained by culturing yeast naturally containing glutamic acid, in a food or drink.

For example, PTL (Patent Literature) 1 describes a sweetness improver containing a yeast extract as an active component, wherein the yeast extract contains sodium 5'-inosinate and/or sodium 5'-adenylate, sodium 5'-guanylate, sodium 5'-uridylate and sodium 5'-cytidylate at a concentration of 1% to 15%, respectively, and sodium glutamate at a concentration of 1% to 20%.

PTL 2 describes a method for producing a yeast extract containing at least 3% of intracellular free glutamine-derived glutamic acid relative to the extract solids, which includes a step of digesting a yeast containing 15 mg or more of free glutamine per 1 g of dried biomass.

PTL 3 describes a yeast extract obtained by digestion or decomposition of a yeast, wherein when the yeast extract is allowed to pass through a filter membrane having a diameter of 1 μm and the permeate is subjected to gel filtration, and when peptides in the fractionated effluent are detected by absorption spectrophotometry at 220 nm, a portion of peptides having a molecular weight of 10,000 or higher is 10% or higher based on the total amount of all the detected peptides.

PTL 4 describes a yeast extract with a high glutamic acid content, which contains 13% by weight or more of L-glutamic acid (as a Na salt).

PTL 5 describes a yeast extract wherein the content of free amino acid is 25% by weight or more, and the total content of nucleic acid-based gustatory components is 2% by weight or more.

PTL 6 describes a seasoning composition containing nucleic acid-based gustatory substances, glutamic acids, potassium and lactic acid, sodium lactate or potassium lactate, wherein a molar ratio of nucleic acid-based gustatory substance:glutamic acid is in the range of 1:2 to 40, and a molar ratio of (nucleic acid-based gustatory substances+glutamic acids):potassium:(lactic acid, sodium lactate or potassium lactate) is in the range of 1:5 to 80:10 to 80.

PTL 7 describes a yeast which is resistant to a glutamic acid antagonistic growth inhibitor and accumulates glutamic acid in biomass.

PTL 8 describes a method for producing a yeast extract, which uses *Yarrowia lipolytica*, a yeast having resistance to Nystatin, a drug which obstructs the structure and function of the cell membrane, and which has a capacity to accumulate 530 mg/L or more of L-glutamic acid in biomass.

RELATED ART LITERATURE

Patent Literature

[PTL 1]: Japanese Patent No. 3088709
[PTL 2]: JP-A No. 2002-171961
[PTL 3]: JP-A No. 2005-102549
[PTL 4]: JP-A No. 2006-129835
[PTL 5]: JP-A No. 2007-49989
[PTL 6]: JP-A No. H05-227911
[PTL 7]: JP-A No. H09-294581
[PTL 8]: Japanese Patent No. 3896606

SUMMARY OF INVENTION

Technical Problem

However, the related art method frequently suffers from complexity of the operation such as a need for decomposition treatment including acid-hydrolysis (HVP) treatment. Further, the free glutamic acid content of currently commercially available yeast extracts is typically about 10%, so there is a need for a method of producing a yeast extract with a higher concentration of glutamic acid.

PTL 1 describes a yeast extract containing sodium glutamate at a concentration of 1% to 20%. However, yeast extract as a commercial product contains sodium glutamate at a concentration of 5.0%, which is practically used, and there is no disclosure of a yeast extract product containing 5.0% or more of sodium glutamate.

PTL 2 suffers from complexity of the operation due to carrying out gene manipulation, and poor safety, palatability or the like in terms of food.

PTL 3 describes containing 10% or more of sodium glutamate (soda) per solids, but there is no disclosure of Working Examples specifically showing this.

PTL 4 suffers from complexity of the operation such as enzymatic treatment.

PTL 5 suffers from complexity of the operation such as use of enzymes as well as only about 13% of glutamic acid per dried powder.

PTL 6 is merely external addition of glutamic acid.

PTL 7 suffers from a low content of glutamic acid per dried biomass weight.

PTL 8 suffers from complexity of the operation such as impartment of drug resistance to a parent strain.

The present invention has been made in view of the above situation, and it is an object of the present invention to provide a method for producing a yeast with a high glutamic acid content, which contains a higher concentration of glutamic acid, particularly free glutamic acid, as compared to the related art, a yeast with a high glutamic acid content, a yeast extract with a high glutamic acid content, and a glutamic acid-containing food or drink.

DETAILED DESCRIPTION OF THE INVENTION

As a result of intensive studies to accomplish the object, the inventors of the present invention found that a content of glutamic acid in yeast, particularly a content of free glutamic acid is increased by elevating a pH of a culture solution to a specific pH (shift to an alkaline range) during the culture of a yeast in a stationary growth phase. In addition, the inventors of the present invention found that a yeast extract with a high glutamic acid content can be produced by preparing a yeast extract using this yeast. The present invention has been completed based on these findings. That is, the present invention adopts the following configurations.

(1) A method for culturing a yeast, including a step of subjecting a yeast in a stationary growth phase to liquid culture under the conditions that the pH of a liquid medium is 7.5 or higher and lower than 11.

(2) The method for culturing a yeast according to (1), wherein the step of liquid culture includes:
a step of adjusting the pH of a liquid medium to 7.5 or higher and lower than 11 after the growth of a yeast enters a stationary phase; and
a step of further culturing the yeast within the same range of pH.

(3) The method for culturing a yeast according to (2), wherein the step of adjusting the pH of a liquid medium to 7.5 or higher and lower than 11 is a step of adding an alkaline substance to the liquid medium.

(4) The method for culturing a yeast according to (1), wherein, in the step of liquid culture, a portion of the cultured yeast is recovered and the content of free glutamic acid in the yeast is intermittently measured.

(5) The method for culturing a yeast according to any one of (1) to (4), wherein the yeast is *Saccharomyces cerevisiae* or *Candida utilis*.

(6) A method for producing a yeast, comprising a step of recovering yeast cultured by the culture method according to any one of (1) to (5).

(7) A yeast obtained by the yeast culture method according to any one of (1) to (5) or obtained by the production method according to (6).

(8) The yeast according to (7), wherein the content of free glutamic acid is from 2.3% by weight to 10.0% by weight per dried yeast biomass.

(9) The yeast according to (8), wherein the content of free glutamic acid is from 4.0% by weight to 10.0% by weight per dried yeast biomass.

(10) A yeast extract obtained by extraction from the yeast according to (7).

(11) The yeast extract according to (10), wherein the content of free glutamic acid in the yeast extract is from 7% by weight to 35% by weight per dried weight.

(12) The yeast extract according to (11), wherein the content of free glutamic acid in the yeast extract is from 20% by weight to 35% by weight per dried weight.

(13) A yeast extract with a free glutamic acid content of 20% by weight to 35% by weight per dried weight.

(14) A yeast with a free glutamic acid content of 4.0% by weight to 10.0% by weight per dried yeast biomass.

(15) A seasoning composition comprising the yeast extract according to any one of (10) to (13).

(16) A food or drink comprising the yeast according to any one of (7) to (9) and (14), the yeast extract according to any one of (10) to (13), or the seasoning composition according to (15).

Advantageous Effects of Invention

Through the method for producing a yeast with a high glutamic acid content in accordance with the present invention, a yeast with a high glutamic acid content wherein the content of glutamic acid, particularly the content of free glutamic acid is significantly increased can be conveniently produced by merely shifting the pH of a liquid medium for a yeast in a stationary growth phase to an alkali range.

By carrying out an extraction operation from the yeast with a high glutamic acid content in accordance with the present invention, a yeast extract with a high glutamic acid content containing glutamic acid, particularly free glutamic acid at a high concentration is obtained.

DESCRIPTION OF EMBODIMENTS

The culture method of a yeast in accordance with the present invention includes a step of subjecting a yeast in a stationary growth phase to liquid culture under the conditions that the pH of a liquid medium is 7.5 or higher and lower than 11. By carrying out this culture method, it is possible to obtain a yeast with a high glutamic acid content.

Hereinafter, embodiments of the present invention will be described in detail.

The yeast is any yeast as long as it is a unicellular fungus. Specific examples of the yeast include fungi belonging to the genus *Saccharomyces*, fungi belonging to the genus *Shizosaccharomyces*, fungi belonging to the genus *Pichia*, fungi belonging to the genus *Candida*, fungi belonging to the genus *Kluyveromyces*, fungi belonging to the genus *Williopsis*, fungi belonging to the genus *Debaryomyces*, fungi belonging to the genus *Galactomyces*, fungi belonging to the genus *Torulaspora*, fungi belonging to the genus *Rhodotorula*, fungi belonging to the genus *Yarrowia*, and fungi belonging to the genus *Zygosaccharomyces*.

Among these, from the viewpoint of edibility, *Candida tropicalis*, *Candida lipolytica*, *Candida utilis*, *Candida sake*, *Saccharomyces cerevisiae* or the like is preferable, and commonly used *Saccharomyces cerevisiae* or *Candida utilis* is more preferable.

For practical application of the present invention, the yeast is cultured until a stationary phase in a liquid medium containing a carbon source, a nitrogen source, an inorganic salt, and the like, and the yeast is then subjected to liquid culture under the conditions that the pH of a liquid medium for the yeast in a stationary growth phase is 7.5 or higher and lower than 11.

The medium composition for these fungal strains is not particularly limited, and may employ a medium composition used in the established method. For example, one or two or more kinds selected from the group consisting of glucose, sucrose, acetic acid, ethanol, molasses, sulfurous acid pulp waste liquor, and the like used in conventional culture of microorganisms are used as a carbon source. One or two or more kinds selected from the group consisting of an inorganic salt such as urea, ammonia, ammonium sulfate, ammonium chloride or ammonium phosphate and a nitrogen-containing organic substance such as corn steep liquor (CSL), casein, yeast extract or peptone are used as a nitrogen source. In addition, a phosphoric acid component, a potassium component, or a magnesium component may be added to the medium. For the purpose of this, a conventional industrial raw material, such as calcium superphosphate, ammonium phosphate, potassium chloride, potassium hydroxide, magnesium sulfate or magnesium chloride, is used. Further, an inorganic salt may also be used such as zinc, copper, manganese or iron ions. In addition, vitamins, nucleic acid-related substances or the like may be added.

The culture mode may be any of batch culture, feeding culture and continuous culture. However, feeding culture or continuous culture is adopted from an industrial viewpoint.

The culture conditions in a logarithmic growth phase or the culture conditions before pH adjustment may follow the common culture conditions of yeast. For example, the temperature is in the range of 20° C. to 40° C., preferably 25° C. to 35° C., and the pH is in the range of 3.5 to 7.5, particularly preferably 4.0 to 6.0. In addition, aerobic conditions are preferable.

Further, the culture is preferably carried out while aeration and stirring are carried out. Aeration volume and stirring conditions may be appropriately determined taking into consideration culture volume and time and an initial fungal concentration. For example, aeration may be carried out at about 0.2 V.V.M. to 2 V.V.M. (Volume per volume per minutes), and stirring may be carried out at about 50 rpm to 800 rpm.

The liquid culture method of a yeast in a stationary growth phase under the conditions that the pH of a liquid medium is 7.5 or higher and lower than 11 is not particularly limited. Examples of the method of adjusting a pH include a method of adjusting the pH of a liquid medium to 7.5 or higher and lower than 11 when the cultured yeast enters a stationary phase, a method of adjusting a pH by adding an alkaline substance to a liquid medium, and a method of subjecting a liquid medium to alkali shift by adding urea or the like in advance to the medium, so that a pH naturally becomes 7.5 or higher and lower than 11 as the culture time passes.

The amount of an alkaline substance added to the medium is not limited as long as a pH is in the above-specified range. From the viewpoint of not excessively diluting the medium, and having no adverse effects on the production of glutamic acid during subsequent culture, the amount of an alkaline substance is preferably 5% or less relative to the medium. For example, the amount of urea as an alkaline substance is not particularly limited and depends on a biomass concentration of yeast to be cultured, but is preferably in the range of about 0.5% to 5% relative to the medium.

The method of adjusting the pH of a liquid medium to 7.5 or higher and lower than 11 when the cultured yeast enters a stationary phase is not particularly limited. For example, an alkaline substance is appropriately added such that the pH of a liquid medium is adjusted to 7.5 or higher and lower than 11, and preferably 7.5 or higher and 10 or lower.

The pH adjustment may be carried out at any time as long as a yeast is in a stationary phase, but is preferably carried out immediately after the yeast enters a stationary phase. This is because a concentration of free glutamic acid in yeast can be sufficiently enhanced and the time required for the completion of the overall processes can be reduced. If the pH of a liquid medium for a yeast in a logarithmic growth phase is set to 7.5 or higher and lower than 11, the growth of yeast is inhibited and the content of free glutamic acid in yeast is not increased, therefore, it is not preferable.

Further, when a yeast under culture shifts to a stationary phase from a logarithmic growth phase, the yeast gradually shifts from a logarithmic growth state to a stationary state and then completely enters the stationary state, but the time of gradually approaching the complete stationary state when the yeast completely reaches the stationary state from the logarithmic growth phase is also included in the stationary phase of the present invention.

The alkaline substance is not particularly limited and examples thereof include the following components.

These include an inorganic alkali such as $NH_4OH$ (aqueous ammonia), ammonia gas, sodium hydroxide, potassium hydroxide, calcium hydroxide or magnesium hydroxide, an alkaline base such as sodium carbonate or potassium carbonate, an organic alkali such as urea, and the like.

Among these, aqueous ammonia, ammonia gas or urea is preferable.

When a yeast in a stationary phase is cultured in a liquid medium with a pH of 7.5 or higher and lower than 11, the temperature and other conditions may follow the common culture conditions of yeast. For example, the temperature is in the range of 20° C. to 40° C., preferably 25° C. to 35° C. The culture time is preferably immediately after the pH adjustment to 24 hours, more preferably from 1 hour to 15 hours, still more preferably 3 hours to 12 hours, and particularly preferably 3 hours to 6 hours.

The content of free glutamic acid in yeast after shift of a pH to 7.5 or higher and lower than 11 tends to increase over culture time, and after reaching the peak, tends to decrease. In addition, the content of free glutamic acid in yeast depends on the conditions such as biomass concentration of yeast to be cultured, pH, and temperature. This is believed to be due to the fact that excessively long-term culture under alkali conditions results in excessively heavy effects of alkali on yeast. Therefore, the present invention is configured such that a portion of the cultured yeast is recovered after pH shift and the content of free glutamic acid in yeast is intermittently measured, preferably at regular intervals of time, although the optimal culture time may be appropriately selected for every set of culture conditions, particularly every pH after alkali shift.

That is, it was confirmed that a yeast with very high free glutamic acid content, that is, a free glutamic acid content of 2.3% by weight to 10.0% by weight per weight of dried yeast biomass, can be obtained by completing the culture at the peak and recovering the yeast. When culturing and producing under more preferable conditions, a yeast containing free glutamic acid in the range of 4.0% by weight to 10.0% by weight per weight of dried yeast biomass can be obtained. In addition, it was confirmed that a yeast extract with a very high glutamic acid content to an extent that has not been reported by the related art, that is, a free glutamic acid content of 20% by weight to 35% by weight per dried weight, can be obtained by preparing a yeast extract using a yeast at the peak.

As described above, in accordance with the production method of the present invention, a yeast with a high free glutamic acid content can be cultured, and a yeast with a very high free glutamic acid content can be produced by appropriately recovering the cultured yeast. Therefore, a yeast extract with a high free glutamic acid content can be prepared from the obtained yeast. Further, it is needless to say that the yeast, yeast extract or the like of the present invention is high in the content of total glutamic acids as well as the content of free glutamic acid.

For example, PTL 1 or the like describes a yeast extract containing 20% by weight of glutamic acid in terms of sodium glutamate (molecular weight of about 169), which corresponds to no more than about 17% by weight in terms of the content of glutamic acid (molecular weight of about 147). It is also obvious from this point that the yeast obtained by the production method of the present invention is a yeast with a high glutamic acid content that has not been reported by the related art.

In the present invention, the term "content of free glutamic acid per dried yeast biomass" means a portion (% by weight) of free glutamic acid contained in solids obtained by drying yeast biomass. In addition, the term "content of free glutamic acid per dried weight of yeast extract" means a portion (% by weight) of free glutamic acid contained in solids obtained by drying yeast extract.

The content of free glutamic acid in yeast biomass or in yeast extract is measured using, for example, a biosensor BF-5 manufactured by Oji Scientific Instruments. This apparatus is an apparatus that quantifies glutamic acid in a solution, using an enzyme electrode which is specifically reactive with glutamic acid, and the present enzyme electrode is not reactive with glutamic acid in a protein or peptide. Therefore, it is possible to selectively quantify only the free glutamic acid by using such an apparatus.

In addition, the content of free glutamic acid may be measured by an automatic amino acid analyzer JLC-500/V manufactured by JEOL Ltd., an analyzer Acquity UPLC manufactured by Waters Corporation (USA), or the like, but the analysis apparatus is not particularly limited.

The method of the present invention enables the production of a yeast containing plenty of glutamic acid, particularly free glutamic acid in biomass. The thus obtained yeast with a high glutamic acid content in accordance with the present invention may contain 2.3% by weight or more, preferably 2.3% by weight to 9.1% by weight, and more preferably 4.0% by weight to 9.1% by weight of free glutamic acid in dried yeast biomass. For example, a yeast containing 2.3% by weight to 7.4% by weight, more preferably 4.0% by weight to 7.4% by weight of free glutamic acid in dried yeast biomass may be obtained.

Therefore, a yeast extract containing plenty of free glutamic acid which is a favorable gustatory component may be conveniently obtained by extracting and preparing a yeast extract from the yeast.

The yeast with a high glutamic acid content produced by the method of the present invention is high in content of free amino acid and is also high in content of free glutamic acid. For example, a yeast extract containing 7% by weight or higher, preferably 7% by weight to 35% by weight, more preferably 12% by weight to 35% by weight, and still more preferably 20% by weight to 35% by weight of yeast biomass-derived free glutamic acid per dried weight in the yeast extract may be obtained by preparing a yeast extract using the yeast with a high glutamic acid content in accordance with the present invention. For example, a yeast extract containing 7% by weight to 30% by weight, more preferably 12% by weight to 30% by weight, still more preferably 20% by weight to 30% by weight of free glutamic acid may also be obtained. Further, a yeast extract containing more than 30% by weight and 35% by weight or less of free glutamic acid may also be obtained.

Accordingly, the yeast extract obtained by the present invention exhibits a very high gustatory property and enables the production of a food or drink having a depth of flavor and richness through application thereof to a food or drink.

Further, the present invention enables the production of a yeast with a high glutamic acid content by a convenient process of merely carrying out alkali shift of a liquid medium. Further, as described above, the medium used is not necessarily a special one, and may be prepared using an inexpensive raw material such as ammonia.

Conventionally, the free glutamic acid content of yeast has been enhanced by means of a recombinant or mutant strain mainly through modification of gene(s) (see PTL 2, 7, 8, or the like). On the other hand, according to the method of the present invention, culturing of a yeast in a stationary phase under alkaline conditions can enhance the content of free glutamic acid in yeast, without modification of gene(s). That is, the present invention is a method capable of enhancing the content of free glutamic acid in yeast, without genetic modification of glutamic acid metabolism and accumulation pathways inherent to yeast. Therefore, the use of the method of the present invention can significantly enhance the content of free glutamic acid in naturally-occurring yeast, without carrying out a gene modification treatment which may deteriorate palatability as a food or drink. Further, it is needless to say that the yeast provided to the method of the present invention may be a naturally-occurring yeast (yeast with no artificial gene modification treatment) or a mutant strain.

Although a yeast with a high glutamic acid content containing a high concentration of glutamic acid in yeast biomass is obtained according to the method of the present invention, a fraction containing glutamic acid may be obtained from a yeast with a high glutamic acid content.

Fractionation of the glutamic acid-containing fraction from a yeast with a high glutamic acid content may be carried out by any method as long as it is a method that is commonly carried out.

Further, a yeast extract with a high glutamic acid content can be prepared from the yeast with a high glutamic acid content cultured by the above-mentioned method. Preparation of the yeast extract with a high glutamic acid content may be carried out by any method as long as it is a method that is commonly carried out. For example, a self-digestion method, an enzymatic decomposition method, an acid decomposition method, an alkali extraction method, a hot water extraction method, or the like may be employed. Further, generally, it is considered that virtually almost the whole quantity of glutamic acid in the yeast extract obtained only by a hot water extraction method is free glutamic acid, unlike the yeast extract obtained by an enzymatic reaction method such as a self-digestion method.

The yeast with a high glutamic acid content in accordance with the present invention is rich in free glutamic acid and as a result, a yeast extract having favorable taste is produced with extraction of a yeast extract only by a hot water treatment.

Conventionally, for the purpose of enhancing a content of gustatory amino acid such as free glutamic acid, a hydrolysis treatment by means of an acid or alkali or the like has been generally carried out using a vegetable or animal protein. However, the protein hydrolysate has a problem associated with incorporation of monochloropropanols (MCP) which are suspected carcinogens.

On the other hand, since the yeast with a high glutamic acid content produced by the method of the present invention is inherently high in content of free glutamic acid, a yeast extract with a sufficiently high content of free glutamic acid can be prepared even without carrying out a decomposition treatment by acid or alkali or the like or an enzymatic treatment after extraction of the yeast by a hot water extraction method or the like. That is, through the use of the yeast with a high glutamic acid content in accordance with the present invention, it is possible to conveniently prepare a yeast extract which is excellent in both taste and safety.

Further, a yeast extract powder with a high glutamic acid content may be obtained by powdering the yeast extract with a high glutamic acid content in accordance with the present invention, and a yeast extract powder containing 7% by weight to 35% by weight of free glutamic acid may be obtained by appropriately selecting a yeast fungus.

Further, dried yeast biomass may be prepared from the yeast with a high glutamic acid content cultured by the above-mentioned method. The preparation of dried yeast biomass may be carried out by any method as long as it is a method that is commonly carried out. A freeze drying method, a spray drying method, a drum drying method, or the like may be adopted from an industrial viewpoint.

Further, the yeast with a high glutamic acid content, dried yeast biomass of the yeast, a yeast extract prepared from the yeast, or the yeast extract powder in accordance with the present invention may be formulated into a seasoning composition. Further, the seasoning composition may be made only of the yeast extract or the like in accordance with the present invention, or otherwise may contain other components such as stabilizer and preservative, in addition to the yeast extract or the like in accordance with the present invention. The seasoning composition may be appropriately used in a variety of foods or drinks, analogously to other seasoning compositions.

Further, the present invention relates to a yeast with a high glutamic acid content obtained by the above-mentioned method, and a food or drink containing a yeast extract with a high glutamic acid content extracted from the yeast with a high glutamic acid content. By the incorporation of the yeast with a high glutamic acid content or the like in accordance with the present invention, it is possible to efficiently produce a food or drink containing a high concentration of glutamic acid.

Such a food or drink may be any one as long as it is a food or drink to which a typical dried yeast, a yeast extract, or a seasoning composition containing them can be added. Examples thereof include alcoholic drinks, cold drinks, fermented foods, seasoning, soups, bread, and confectionery.

In order to produce the food or drink in accordance with the present invention, in the production process of a food or drink, a preparation obtained from the yeast with a high glutamic acid content, or a fraction of the yeast with a high glutamic acid content may be added. In addition, as a raw material, the yeast with a high glutamic acid content may be used as it is.

EXAMPLE 1

Hereinafter, the present invention will be described in more detail with reference to the following Examples, but the present invention is not limited thereto.

According to the method given in the following <1> to <8>, yeast (*Saccharomyces cerevisiae* AB9846 strain) was cultured, and extraction of an extract from the yeast culture solution and glutamic acid analysis were carried out.

<1> Preculture

Two media each made up of the following composition were prepared at a volume of 350 mL (2 L Erlenmeyer flask equipped with baffles).

(Medium Composition)
Molasses: 8%
Urea: 0.6%
$(NH_4)_2SO_4$: 0.16% (ammonium sulfate)
$(NH_4)_2HPO_4$: 0.08% (diammonium hydrogen phosphate)

(Preparation Method)

(1) 167 mL of molasses (sugar content: 36%) was mixed up to make 750 mL in Milli-Q water, and a volume of 350 mL/flask was aliquoted to 2 L Erlenmeyer flasks equipped with baffles.

(2) An autoclaving treatment (121° C., 15 minutes) was carried out.

(3) When the medium was used, a 1/50 volume (each 7 mL) of a nitrogen component mixed liquid (×100) was aseptically added to a medium consisting only of molasses.

(Culture Conditions)
Culture temperature: 30° C.
Shaking: 160 rpm (rotary)
Culture time: 24 hours
(Inoculation volume: 300 mL)

<2> Main Culture

A medium made up of the following composition was prepared at a volume of 2000 mL (set to be 3 L when feeding was completed).

(Medium Composition)
0.18% ammonium chloride (3 L in terms of when feeding was completed): 5.3 g
0.04% $(NH_4)_2HPO_4$ (diammonium hydrogen phosphate, in terms of completed feeding): 1.2 g Subsequently, the culture was carried out under the following conditions.

(Culture Conditions)
Culture temperature: 30° C.
Aeration: 3 L/min
Stirring: 600 rpm
pH control: control of the lower limit: pH 5.0 (by 10% aqueous ammonia), no control of the upper limit
Antifoamer: ADEKANATE stock solution
Feeding medium: molasses (sugar content: 36%), volume: 800 mL (in 1 L medium bottle, finally 8%)

<3> pH Shift

Next, immediately after the cultured yeast entered a stationary phase, a pH of the culture solution was shifted to an alkaline range by aqueous $NH_4OH$ (10%) (hereinafter, referred to as "pH shift") (set to a pH of 7 to 11), and the yeast was further cultured. Yeast culturing was finished 48 hours after the main culture was started.

<4> Harvesting Method of Yeast (1) The culture solution obtained by main culture of yeast was transferred to a 50 mL plastic centrifuge tube (FALCON 2070), followed by centrifugation (3,000 g, 20° C., 5 min, HP-26).

(2) The supernatant was discarded and the pellet was suspended in 20 mL of Milli-Q water, followed by centrifugation (3,000 g, 20° C., 5 min, HP-26). This procedure was repeated twice.

(3) The supernatant was discarded and the pellet was suspended in 20 mL of Milli-Q water.

<5> Measurement of Dried Biomass Weight of Yeast 2 mL of a yeast suspension was placed in a pre-weighed aluminum dish (diameter: 5 cm), followed by drying at 105° C. for 4 hours.

The post-drying weight (weight after drying of yeast) was measured, and the weight of solids (dried yeast biomass weight, unit: g/L) was calculated according to the following equation (1).

$$\text{Weight after drying of yeast} - \text{weight of aluminum dish} = \text{weight of dried yeast biomass} \quad (1)$$

<6> Preparation of Extract Solution by Hot Water Extraction Method (1) The remaining yeast suspension (about 18 mL) was centrifuged (3,000 g, 20° C., 5 min, HP-26).

(2) 1.5 mL of the remaining suspension was transferred to an Eppendorf tube which was then transferred to a block heater, followed by heating at 80° C. for 30 minutes (to make an extract). Alternatively, the suspension-containing tube may be overheated in a hot bath at 100° C. for 10 minutes (to make an extract).

(3) Then, the supernatant (extract solution) was separated by centrifugation (6,000 g, 4° C., 5 minutes).

<7> Measuring Method of Free Glutamic Acid Content

Free glutamic acid in 300 μL of the extract solution was quantified by using a biosensor. According to the measuring method using a biosensor, it is possible to selectively quantify only the free glutamic acid in the extract solution. Specifically, the measurement was carried out for a dilution of the extract solution (appropriately 5-fold diluted) by using BF-5 manufactured by Oji Scientific Instruments, and 1 mM and 5 mM standard solutions were used in the calibration curve.

The results obtained for shifting to pH 7.00, 7.50, 8.00, 9.00, and 11.00 are given in Table 1. With respect to the range of pH 8.00 to 9.00, the results obtained with an interval of change of a pH of 0.25 are given in Table 2. With respect to the range of pH 9.00 to 10.00, the results obtained with an interval of change of a pH of 0.25 are given in Table 3. As demonstrated from the bacterial count data and dried yeast biomass weight data shown in Table 2, pH shift was carried out after the growth of yeast entered the stationary phase.

TABLE 1

| Set pH | | Dried yeast biomass weight (g/L) | Glutamic acid content (% by weight in dried yeast biomass) |
|---|---|---|---|
| | Immediately after inoculation | 1.3 | 1.6 |
| 7.0 | Before pH shift | 34.5 | 2.8 |
| | 6 hours after pH shift | 36.6 | 2.6 |
| 7.5 | Before pH shift | 35.8 | 2.4 |
| | 6 hours after pH shift | 35.2 | 2.7 |
| 8.0 | Before pH shift | 34.4 | 2.4 |
| | 6 hours after pH shift | 33.0 | 2.8 |
| 9.0 | Before pH shift | 38.3 | 2.2 |
| | 6 hours after pH shift | 36.7 | 5.3 |
| 11.0 | Before pH shift | 37.4 | 2.2 |
| | 6 hours after pH shift | 17.7 | 0.0 |

TABLE 2

| Set pH | | Bacterial count (×10$^6$ cells/mL) | Dried yeast biomass weight (g/L) | Glutamic acid content (% by weight in dried yeast biomass) |
|---|---|---|---|---|
| 8.00 | Immediately after inoculation | 76 | 1.3 | 2.5 |
| | Before pH shift | 2160 | 29.5 | 1.7 |
| | 3 hours after pH shift | 2420 | 29.4 | 2.5 |
| 8.25 | Immediately after inoculation | 79 | 1.0 | 2.3 |
| | Before pH shift | 1980 | 30.9 | 2.3 |
| | 3 hours after pH shift | 2140 | 30.3 | 3.4 |
| 8.50 | Immediately after inoculation | 80 | 0.6 | 2.0 |
| | Before pH shift | 2460 | 30.2 | 2.0 |
| | 3 hours after pH shift | 2220 | 30.2 | 3.6 |
| 8.75 | Immediately after inoculation | 88 | 1.0 | 3.1 |
| | Before pH shift | 2180 | 32.2 | 1.9 |
| | 3 hours after pH shift | 2740 | 32.4 | 4.1 |
| 9.00 | Immediately after inoculation | 70 | 1.2 | 2.4 |
| | Before pH shift | 2500 | 32.3 | 1.8 |
| | 3 hours after pH shift | 2360 | 30.7 | 4.0 |

TABLE 3

| Set pH | | Dried yeast biomass weight (g/L) | Glutamic acid content (% by weight in dried yeast biomass) |
|---|---|---|---|
| 9.00 | Immediately after inoculation | 1.2 | 1.3 |
| | Before pH shift | 36.7 | 2.3 |
| | 6 hours after pH shift | 35.1 | 5.7 |
| 9.25 | Immediately after inoculation | 1.0 | 1.8 |
| | Before pH shift | 35.0 | 2.2 |
| | 6 hours after pH shift | 32.4 | 5.1 |
| 9.50 | Immediately after inoculation | 1.1 | 1.3 |
| | Before pH shift | 35.4 | 2.9 |
| | 6 hours after pH shift | 34.2 | 3.7 |
| 9.75 | Immediately after inoculation | 1.3 | 1.3 |
| | Before pH shift | 36.8 | 1.9 |
| | 6 hours after pH shift | 31.7 | 2.6 |
| 10.00 | Immediately after inoculation | 1.1 | 1.2 |
| | Before pH shift | 37.6 | 2.0 |
| | 6 hours after pH shift | 33.1 | 2.3 |

As shown in Table 1, it was confirmed that the content (% by weight) of free glutamic acid in the dried yeast biomass increases at the set pH of 7.5 or higher and lower than 11.0, before pH shift and 6 hours after pH shift. Particularly, at the set pH of 9.0, the content of free glutamic acid increased 2-fold or higher from 2.2% by weight to 5.3% by weight, as a result of pH shift, thus confirming a significant increase in the content of free glutamic acid.

Particularly, when the set pH (pH after pH shift) is in the range of 8.00 to 9.00, it was confirmed, as shown in Table 2, that the higher set pH leads to a higher increase in the content (% by weight) of free glutamic acid in the dried yeast biomass as a result of the pH shift.

On the other hand, as shown in Table 3, when the set pH is in the range of 9.00 to 10.00, it was confirmed that an increase in the content (% by weight) of free glutamic acid in the dried yeast biomass as a result of the pH shift was more significant as the set pH decreases. Particularly, at the set pH of 9.00, the glutamic acid content was increased from 2.3% by weight to 5.7% by weight as a result of the pH shift. In addition, although not shown in the table, at the set pH of 9.00, the content of free glutamic acid in the dried yeast biomass was 4.6% by weight 3 hours after pH shift.

In addition, among these yeasts, it was confirmed that the yeast extract prepared using the yeast after being subjected to the pH shift within the set pH of 7.5 or higher and lower than 11.0 exhibited an increase in the content (% by weight) of glutamic acid per dried weight, as compared to the yeast extract prepared using yeast before being subjected to the pH shift, and a yeast extract with a high content of glutamic acid was obtained by preparing a yeast extract using the yeast produced by the production method of the present invention. For example, with regard to the yeast with the set pH of 9.00 given in Table 1, in the yeast extract prepared from the yeast before being subjected to the pH shift, the content of glutamic acid per dried weight was 22.4% by weight in the yeast extract prepared from the yeast 6 hours after pH shift. In addition, with regard to the yeast with the same set pH of 9.00 (see Table 3), the content of glutamic acid per dried weight was 19.4% by weight in the yeast extract prepared from the yeast cultured for 3 hours after pH shift, and the content of glutamic acid per dried weight was 25.5% by weight in the yeast extract prepared from the yeast cultured for 6 hours after pH shift. In addition, with regard to the yeast with the set pH of 9.25 (see Table 3), the content of glutamic acid per dried weight was 21.3% by weight in the yeast extract prepared from the yeast cultured for 6 hours after pH shift.

From the results above, it was shown that the content of glutamic acid in yeast is increased by the adjustment of the pH to 7.5 or higher and lower than 11 after a stationary phase and the culturing. Particularly, the content of glutamic acid was high at 3 hours to 6 hours after pH adjustment.

EXAMPLE 2

Preculture was carried out in the same manner as in <1> of Example 1, and then main culture was carried out under the following conditions.

Instead of carrying out pH shift after a stationary phase, urea was previously added to the medium of main culture such that a pH was allowed to spontaneously shift, thereby obtaining a yeast with a high glutamic acid content.

First, a medium made up of the following composition was prepared at a volume of 2000 mL (set to be 3 L when feeding was completed).

Figure 1:
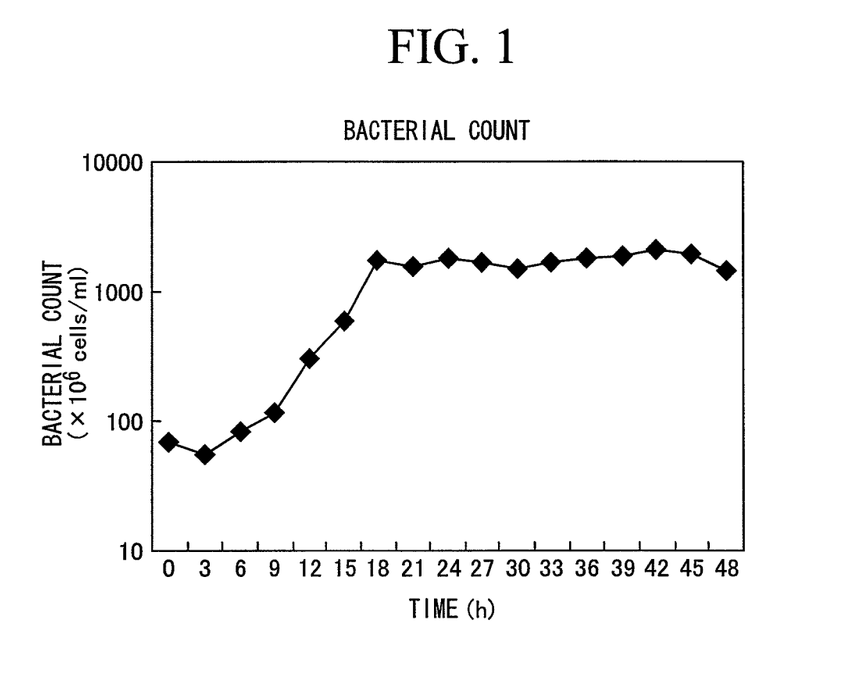
FIG. 1 is a curve showing an increase in bacterial count vs. culture time in Example 2.
Figure 2:
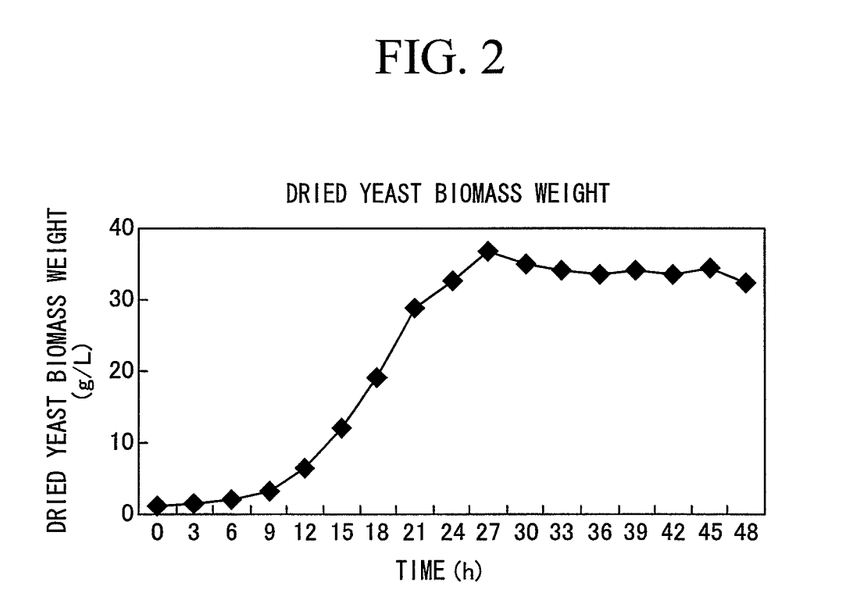
FIG. 2 is a curve showing an increase in dried yeast biomass weight vs. culture time in Example 2.
Figure 3:
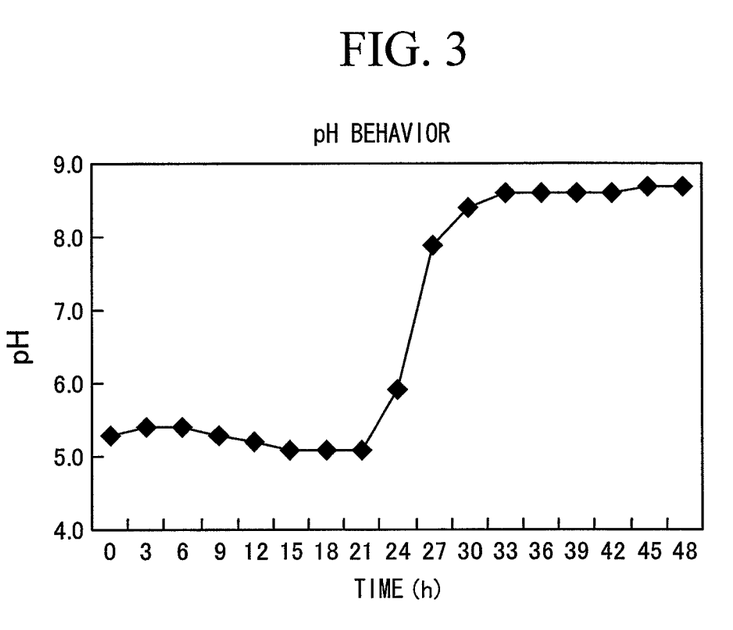
FIG. 3 shows changes in the pH of a liquid medium vs. culture time in Example 2.

(Medium Composition)
0.18% ammonium chloride (3 L in terms of when feeding was completed): 5.3 g
0.04% $(NH_4)_2HPO_4$ (diammonium hydrogen phosphate, in terms of when feeding was completed): 1.2 g
1% urea (3 L in terms of when feeding was completed): 30 g Other conditions were the same as in Example 1. FIG. 1 is a curve showing an increase in bacterial count vs. culture time. FIG. 2 is a curve showing an increase in dried yeast biomass weight vs. culture time. FIG. 3 shows changes in a pH of a culture solution vs. culture time.

As shown in FIG. 1, an increase in the bacterial count ($\times 10^6$ cells/mL) arrived at the stationary state after 18 hours of culture, thus confirming the entrance to a stationary phase. In addition, the dried yeast biomass weight (g/L) arrived at substantially the stationary state after 24 hours of culture, thus confirming a stationary phase of growth. When a pH of the culture solution was measured, as shown in FIG. 3, a pH was shifted to an alkali range (7.5 or higher and lower than 11) after entering the stationary phase of growth. The results are given in Table 4.

TABLE 4

| Time (hours) lapsed | pH | Bacterial count ($\times 10^6$ cells/mL) | Dried yeast biomass weight (g/L) | Glutamic acid content (% by weight in dried yeast biomass) |
|---|---|---|---|---|
| 0 | 5.3 | 69 | 1.3 | 1.7 |
| 3 | 5.4 | 56 | 1.3 | 2.0 |
| 6 | 5.4 | 83 | 2.1 | 2.6 |
| 9 | 5.3 | 118 | 3.2 | 2.5 |
| 12 | 5.2 | 310 | 6.4 | 2.8 |
| 15 | 5.1 | 600 | 12.0 | 2.9 |
| 18 | 5.1 | 1750 | 19.3 | 3.1 |
| 21 | 5.1 | 1540 | 28.8 | 2.7 |
| 24 | 5.9 | 1840 | 32.7 | 2.6 |
| 27 | 7.9 | 1700 | 36.9 | 3.8 |
| 30 | 8.4 | 1510 | 35.1 | 5.8 |
| 33 | 8.6 | 1660 | 34.3 | 6.0 |
| 36 | 8.6 | 1830 | 33.5 | 6.5 |
| 39 | 8.6 | 1870 | 34.3 | 6.7 |
| 42 | 8.6 | 2080 | 33.7 | 7.2 |
| 45 | 8.7 | 1940 | 34.5 | 7.3 |
| 48 | 8.7 | 1470 | 32.4 | 7.4 |

As shown in Table 4, the content of glutamic acid per dried yeast biomass weight became 7.4% by weight when a pH rose, which corresponds to a 2.8-fold increase as compared to 2.6% by weight before a rise of pH.

EXAMPLE 3

Extraction of an extract from the yeast culture solution and glutamic acid analysis were carried out in the same manner as in Example 1, except that the preculture and main culture conditions were the following conditions.

(Medium Composition)
Preculture solution: 150 mL
The supernatant was removed from the preculture solution obtained in the same manner as in the preculture of Example 1, and a concentrate where a yeast concentration was concentrated to 15% to 20% was used as a preculture solution.
Water: 2000 mL
$H_2SO_4$ (97%): 1.33 mL
Molasses (sugar content: 36%): 6.7 mL
$(NH_4)_2HPO_4$: 0.06%
(Culture Conditions)
Culture temperature: 32° C.
pH: 0 hour to 15.5 hours: Not adjusted
Stirring: 600 rpm Subsequently, the culture was carried out under the following conditions.

After 15.5 hours: pH shift was carried out with aqueous ammonia
Stirring: 600 rpm
Feeding medium: molasses (sugar content: 36%): 870 mL
$NH_4OH$ (10%): 100 to 200 mL
Phosphoric acid (85%): 5 to 20 (g)

Yeast was cultured, and pH shift was carried out by aqueous $NH_4OH$ after 15.5 hours, followed by continuation of culture. The results obtained are given in Table 5.

TABLE 5

| Set pH | | Dried yeast biomass weight (g/L) | Glutamic acid content (% by weight in dried yeast biomass) |
|---|---|---|---|
| 9.0 | Immediately after inoculation | 15.2 | 2.3 |
| | Before pH shift | 65.3 | 3.0 |
| | 6 hours after pH shift | 63.3 | 9.0 |

As shown in Table 5, it was confirmed that the content (% by weight) of free glutamic acid in the dried yeast biomass increased at the set pH of 9.0, before pH shift and 6 hours after pH shift. The glutamic acid content of 9.0% by weight was about 25% in terms of glutamic acid content in the yeast extract.

The composition of the medium was different in comparison with Example 1, and it was confirmed that any medium composition is capable of increasing the content of glutamic acid in a pH-dependent manner.

EXAMPLE 4

Extraction of an extract from the yeast culture solution and glutamic acid analysis were carried out in the same manner as in Example 3, except that a feeding medium for use in main culture was set to satisfy the following conditions, and the culture time after pH shift was 3 hours. The results obtained are given in Table 6.

Feeding medium: molasses (sugar content: 36%): 760 mL to 870 mL

NH$_4$OH (10%): 100 mL to 200 mL

Phosphoric acid (85%): 5 to 20 (g)

TABLE 6

| Example No. | Set pH | | Dried yeast biomass weight (g/L) | Glutamic acid content (% by weight in dried yeast biomass) |
|---|---|---|---|---|
| 4-1 | 9.0 | Before pH shift | 55.8 | 2.25 |
|  |  | 3 hours after pH shift | 52.2 | 8.44 |
| 4-2 | 9.0 | Before pH shift | 48.1 | 2.52 |
|  |  | 3 hours after pH shift | 47.0 | 8.06 |
| 4-3 | 9.0 | Before pH shift | 50.3 | 2.48 |
|  |  | 3 hours after pH shift | 48.7 | 8.45 |
| 4-4 | 9.0 | Before pH shift | 49.7 | 2.29 |
|  |  | 3 hours after pH shift | 53.7 | 9.13 |

As shown in Table 6, the contents (% by weight) of free glutamic acid in the dried yeast biomass were 8.44% by weight (Example 4-1), 8.06% by weight (Example 4-2), 8.45% by weight (Example 4-3), and 9.13% by weight (Example 4-4), respectively. On the other hand, the contents of free glutamic acid in the yeast extract prepared using such a yeast were 33.2% by weight (Example 4-1), 33.3% by weight (Example 4-2), 28.2% by weight (Example 4-3), and 27.1% by weight (Example 4-4), respectively.

From these results, it is obvious that by subjecting a yeast in a stationary phase to pH shift, it is possible to obtain a yeast with a very high content of free glutamic acid, that is, a content of 8% by weight or higher in the dried yeast biomass, and it is possible to prepare a yeast extract containing plenty of free glutamic acid not exhibited by the related art, that is, a free glutamic acid content of 30% by weight or higher.

EXAMPLE 5

Subsequently, the culture was carried out in the same manner as in Example 1 using yeast (*Candida utilis* JCM1624 strain) as a strain, and extraction of an extract from the yeast culture solution and glutamic acid analysis were carried out. The results are given in Table 7.

TABLE 7

| Set pH | | Dried yeast biomass weight (g/L) | Glutamic acid content (% by weight in dried yeast biomass) |
|---|---|---|---|
| 9.0 | Immediately after inoculation | 3.8 | 1.7 |
|  | Before pH shift | 44.6 | 2.2 |
|  | After pH shift | 46.1 | 2.6 |

From the results above, yeast (*Candida utilis* JCM1624 strain) also exhibited a significant increase in the content of glutamic acid in the yeast, as a result of carrying out pH shift after a stationary phase.

EXAMPLE 6

Next, for the yeast extract prepared from the yeast (set pH of 9.0) produced in the same manner as in Example 1 except that the culture time after pH shift was 3 hours, the free glutamic acid content and the total free amino acid content per dried weight were measured. In addition, a measurement of free amino acids such as free glutamic acid was carried out using an analyzer Acquity UPLC manufactured by Waters Corporation, according to an AccQ-Tag Ultra labeling method. The results measured are given in Table 8. In Table 8, the term "glutamic acid content" means the free glutamic acid content per dried weight of a yeast extract, and the term "total amino acid content" means the total content of free amino acids per dried weight of a yeast extract.

TABLE 8

|  | Before shift | 3 hours after shift |
|---|---|---|
| Glutamic acid content (% by weight in extract) | 6.9 | 26 |
| Total amino acid content (% by weight in extract) | 11.4 | 43 |

As shown in Table 8, the free glutamic acid contents before and after pH shift were 6.9% by weight and 26% by weight, respectively, thus representing an approximate 3.7-fold increase. On the other hand, the total free amino acid content was increased from 11.4% by weight to 43% by weight.

EXAMPLE 7

Subsequently, with regard to the yeast extract prepared from the yeast (pH 9.0) produced in the same manner as in Example 1 and commercially available yeast extracts (Comparative Examples 1 to 8), the free glutamic acid content and the total free amino acid content per dried weight of extract were measured and compared. In addition, a measurement of free amino acids such as free glutamic acid was carried out in the same manner as in Example 6. The free glutamic acid content (% by weight) and the total free amino acid content (% by weight) per dried weight of each yeast extract obtained as the measurement results are given in Table 9. In Table 9, the term "glutamic acid content" means the free glutamic acid content per dried weight of a yeast extract, and the term "total amino acid content" means the total content of free amino acids per dried weight of a yeast extract.

TABLE 9

| Sample | Example 7 | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|
| Content in extract | | A company product | B company product | C company product | D company product | E company product | F company product | G company product | H company product |
| Glutamic acid (% by weight) | 29.1 | 5.6 | 0.1 | 8.0 | 3.4 | 3.2 | 0.5 | 9.5 | 9.5 |
| Total amino acid (% by weight) | 60.2 | 8.6 | 5.6 | 11.1 | 8.8 | 9.9 | 3.6 | 21.0 | 17.0 |

From the results above, the free glutamic acid content of the yeast extract in accordance with the present invention was very high, that is, 29.1% by weight. The yeast extract containing free glutamic acid at a very high concentration of about 30% by weight as described above has not been reported by the related art. These results suggest that the yeast extract of the present invention is preferable as a seasoning.

EXAMPLE 8

Using a yeast extract powder (derived from *Saccharomyces cerevisiae* AB9846 strain, glutamic acid content of 23% by weight) obtained by powdering the yeast extract prepared from the yeast (pH 9.0) adjusted in the same manner as in Example 1, a bean paste soup and a consomme soup were prepared. The blending amount of the yeast extract for the bean paste soup and the consomme soup was 0.2%.

Using MEAST POWDER N (manufactured by Asahi Food & Healthcare Co., Ltd., glutamic acid content: 4% by weight) as a Comparative Example, a bean paste soup and a consomme soup were prepared in the same manner as above. Sensory evaluation was carried out according to the following method.

(Evaluation Method)

With the blind 2-point comparison by 10 special panelists, a comparative sensory test was carried out. A t-test was carried out in the form of a pair of comparative tests.

(Evaluation Criteria)

3 items of salty taste (salt-reducing effect), umami and savory taste were evaluated in terms of 5 stages as follows, by taking a bean paste soup or a consomme soup serving as a reference to be 0.

"Strong"=+2,
"Slightly strong"=+1,
"Not belonging to "strong or weak""=0,
"Slightly weak"=−1,
"Weak"=−2.

The results for the bean paste soup are given in Table 10, and the results for the consomme soup are given in Table 11.

TABLE 10

| | | Panel | | | | | | | | | | | |
|---|---|---|---|---|---|---|---|---|---|---|---|---|---|
| Sample | Item | Panel A | Panel B | Panel C | Panel D | Panel E | Panel F | Panel G | Panel H | Panel I | Panel J | Average value | Standard deviation |
| Examples | Salty taste | −1 | 1 | 1 | −1 | −1 | 1 | 0 | 0 | 0 | 1 | 0.10 | 0.88 |
| | Umami | 0 | 0 | 1 | 2 | −1 | 0 | 1 | 1 | 1 | −1 | 0.40 | 0.97 |
| | Savory taste | 0 | 2 | 0 | 1 | 0 | 0 | 1 | 2 | 1 | 1 | 0.80 | 0.79 |
| Meast powder N (Comparative Examples) | Salty taste | 0 | 0 | 1 | −2 | 0 | −1 | 0 | 0 | −1 | 0 | −0.30 | 0.82 |
| | Umami | 1 | 0 | 0 | 1 | −1 | −1 | 1 | 0 | −1 | 0 | 0.00 | 0.82 |
| | Savory taste | 1 | 2 | 0 | 0 | −1 | 0 | 0 | 0 | 0 | 0 | 0.20 | 0.79 |

Paired t-test of data
Salty taste: p = 0.11
Umami: p = 0.11
Savory taste: p = 0.03*

TABLE 11

| | | Panel | | | | | | | | | | | |
|---|---|---|---|---|---|---|---|---|---|---|---|---|---|
| Sample | Item | Panel A | Panel B | Panel C | Panel D | Panel E | Panel F | Panel G | Panel H | Panel I | Panel J | Average value | Standard deviation |
| Examples | Salty taste | 1 | 1 | 1 | 1 | 0 | −1 | 1 | 0 | 0 | 1 | 0.50 | 0.71 |
| | Umami | 1 | 0 | 1 | 2 | 1 | −1 | 2 | 2 | 0 | 1 | 0.90 | 0.99 |
| | Savory taste | 1 | 0 | 0 | 2 | 1 | 0 | 0 | 0 | 0 | 1 | 0.50 | 0.71 |
| Meast powder N (Comparative Examples) | Salty taste | 0 | −1 | 0 | −1 | 1 | 1 | 0 | 0 | 1 | −1 | 0.00 | 0.82 |
| | Umami | 1 | −1 | 0 | −1 | 0 | 1 | 1 | 0 | 0 | −1 | 0.00 | 0.82 |
| | Savory taste | 1 | −1 | 1 | 1 | 1 | 1 | 0 | 0 | 1 | −1 | 0.40 | 0.84 |

Paired t-test of data
Salty taste: p = 0.15
Umami: p = 0.03*
Savory taste: p = 0.38

From the results of Table 10, the bean paste soup exhibited a difference in the average values of salty taste and umami, and a significant difference in the savory taste. From the results of Table 11, the consomme soup exhibited a difference in the average values of salty taste and savory taste, and a significant difference in the umami. This is believed to be due to the fact that the yeast extract of the present invention has a significantly higher content of glutamic acid than those of the related art.

EXAMPLE 9

Since yeasts other than *Saccharomyces cerevisiae* AB9846 strain and *Candida utilis* JCM1624 strain are also obtained with an increased content of glutamic acid in yeast, by carrying out pH shift after a stationary phase, 10 strains belonging to the genus *Saccharomyces*, 4 strains belonging to the genus *Candida*, and 2 strains belonging to the genus *Kluyveromyces* were cultured in the same manner as in Example 1, followed by measurement of glutamic acid contents. Specifically, the culture and measurement of glutamic acid contents were carried out for *Saccharomyces cerevisiae* (brewer's yeast) AB1 strain, *Saccharomyces cerevisiae* (Kyokai wine No. 4) AB2 strain, *Saccharomyces cerevisiae* (Kyokai No. 5 yeast) AB3 strain, (wine yeast) AB4 strain belonging to the genus *Saccharomyces*, *Saccharomyces cerevisiae* (baker's yeast) AB5 strain, *Saccharomyces cerevisiae* (baker's yeast) AB6 strain, (whiskey yeast) AB7 strain belonging to the genus *Saccharomyces*, *Saccharomyces cerevisiae* AB8 strain, *Saccharomyces sake* (Kyokai No. 6 yeast) AB9 strain, *Saccharomyces bayanus* AB10 strain, *Candida utilis* (IAM0626) AB11 strain, *Candida utilis* (IFO0639) AB 12 strain, *Candida utilis* (JCM2287 is a parent strain) AB13 strain, *Candida utilis* (JCM2287 is a parent strain) AB14 strain, *Kluyveromyces lactis* (IFO1090) AB15 strain, and *Kluyveromyces lactis* AB 16 strain. In addition, the culture and measurement of glutamic acid contents were also carried out for *Saccharomyces cerevisiae* AB9846 strain as a control.

Specifically, main culture of each yeast strain precultured in a molasses medium (8% molasses, 0.6% urea, 0.16% ammonium sulfate, and 0.08% diammonium hydrogen phosphate) was carried out in a medium (0.18% ammonium chloride, 0.04% diammonium hydrogen phosphate), using molasses (sugar content: 36%), a volume of 800 mL (in 1 L medium bottle, finally 8%) as a feeding medium. The culture temperature and the aeration/stirring conditions were the same as in Example 1.

Immediately after the cultured yeast entered a stationary phase, pH shift was carried out by aqueous $NH_4OH$ (10%) (set pH of 7 to 11), and yeast was further cultured. Yeast culturing was finished 48 hours after the main culture was started. From the harvested yeast, dried yeast biomass and yeast extract were prepared in the same manner as in Example 1, and amounts of free glutamic acid contained therein were respectively measured.

The measured results of the content (% by weight) of free glutamic acid in the dried yeast biomass are given in Table 12, and the measured results of the content (% by weight) of free glutamic acid in the yeast extract are given in Table 13. With regard to test Nos. 6 to 10, the content of glutamic acid before a rise of pH was not measured.

TABLE 12

| Test No. | Strain | Species | Glutamic acid content (% by weight) before pH shift | Glutamic acid content (% by weight) after pH shift | Glutamic acid content ratio before and after pH shift |
|---|---|---|---|---|---|
| 1 | AB1 | *Saccharomyces cerevisiae* (brewer's yeast) | 2.0 | 6.3 | 3.15 |
| 2 | AB2 | *Saccharomyces cerevisiae* (Kyokai wine No. 4) | 1.5 | 2.7 | 1.8 |
| 3 | AB3 | *Saccharomyces cerevisiae* (Kyokai No. 5 yeast) | 2.7 | 5.2 | 1.9 |
| 4 | AB4 | Genus *Saccharomyces* (wine yeast) | 1.8 | 4.4 | 2.4 |
| 5 | AB5 | *Saccharomyces cerevisiae* (baker's yeast) | 2.5 | 4.7 | 1.9 |
| 6 | AB6 | *Saccharomyces cerevisiae* (baker's yeast) | — | 4.6 | — |
| 7 | AB7 | Genus *Saccharomyces* (whiskey yeast) | — | 5.3 | — |
| 8 | AB8 | *Saccharomyces cerevisiae* | — | 5.4 | — |
| 9 | AB9 | *Saccharomyces sake* (Kyokai No. 6 yeast) | — | 5.3 | — |
| 10 | AB10 | *Saccharomyces bayanus* | — | 6.4 | — |
| 11 | AB11 | *Candida utilis* (IAM0626) | 1.3 | 1.7 | 1.3 |
| 12 | AB12 | *Candida utilis* (IFO0639) | 2.0 | 4.0 | 2.0 |
| 13 | AB13 | *Candida utilis* (JCM2287 is a parent strain) | 0.3 | 0.5 | 1.8 |
| 14 | AB14 | *Candida utilis* (JCM2287 is a parent strain) | 0.4 | 1.1 | 3.1 |
| 15 | AB15 | *Kluyveromyces lactis* (IFO1090) | 0.2 | 0.9 | 5.4 |
| 16 | AB16 | *Kluyveromyces lactis* | 0.3 | 2.9 | 11.0 |
| 17 | AB9846 | *Saccharomyces cerevisiae* (control) | 2.7 | 5.9 | 2.2 |

TABLE 13

| Test No. | Strain | Species | Glutamic acid content (% by weight) before pH shift | Glutamic acid content (% by weight) after pH shift | Glutamic acid content ratio before and after pH shift |
|---|---|---|---|---|---|
| 1 | AB1 | *Saccharomyces cerevisiae* (brewer's yeast) | 7.8 | 26.8 | 3.4 |
| 2 | AB2 | *Saccharomyces cerevisiae* (Kyokai No. wine 4) | 9.5 | 12.6 | 1.3 |
| 3 | AB3 | *Saccharomyces cerevisiae* (Kyokai No. 5 yeast) | 8.5 | 18.0 | 2.1 |

TABLE 13-continued

| Test No. | Strain | Species | Glutamic acid content (% by weight) before pH shift | Glutamic acid content (% by weight) after pH shift | Glutamic acid content ratio before and after pH shift |
|---|---|---|---|---|---|
| 4 | AB4 | Genus Saccharomyces (wine yeast) | 10.2 | 17.8 | 1.7 |
| 5 | AB5 | Saccharomyces cerevisiae (baker's yeast) | 9.9 | 17.2 | 1.7 |
| 6 | AB6 | Saccharomyces cerevisiae (baker's yeast) | — | 24.6 | — |
| 7 | AB7 | Genus Saccharomyces (whiskey yeast) | — | 29.4 | — |
| 8 | AB8 | Saccharomyces cerevisiae | — | 22.4 | — |
| 9 | AB9 | Saccharomyces sake (Kyokai No. 6 yeast) | — | 28.5 | — |
| 10 | AB10 | Saccharomyces bayanus | — | 28.8 | — |
| 11 | AB11 | Candida utilis (IAM0626) | 4.1 | 6.4 | 1.6 |
| 12 | AB12 | Candida utilis (IFO0639) | 6.3 | 12.7 | 2.0 |
| 13 | AB13 | Candida utilis (JCM2287 is a novel strain) | 1.2 | 3.3 | 2.8 |
| 14 | AB14 | Candida utilis (JCM2287 is a novel strain) | 1.1 | 4.5 | 4.1 |
| 15 | AB15 | Kluyveromyces lactis (IFO1090) | 1.2 | 3.2 | 2.6 |
| 16 | AB16 | Kluyveromyces lactis | 1.3 | 12.4 | 9.4 |
| 17 | AB9846 | Saccharomyces cerevisiae (control) | 10.2 | 21.1 | 2.1 |

As shown in Table 12 and Table 13, it was confirmed that all strains exhibit a steep increase in the content of free glutamic acid after a rise of pH, as compared to before a rise of pH. Further, with regard to test Nos. 6 to 10, although the content of glutamic acid before a rise of pH was not measured, since the content of free glutamic acid per dried yeast biomass was higher than 4.5% by weight in any strains and the content of free glutamic acid in the yeast extract was significantly higher than 20% by weight, it is believed that the content of free glutamic acid was significantly increased by carrying out pH shift after a stationary phase. From these results, it is obvious that an increasing effect of glutamic acid content according to the method of the present invention is displayed in various yeasts without being limited to a specific strain, and such an effect is displayed if the yeast strain is at least a strain belonging to the genus *Saccharomyces* or a strain belonging to the genus *Candida*.

INDUSTRIAL APPLICABILITY

Since a yeast maintaining glutamic acid therein at a high concentration can be obtained by the method for producing a yeast with a high glutamic acid content in accordance with the present invention, such a yeast can be used in the food field such as preparation of yeast extracts.

We claim:

1. A method for culturing a yeast, comprising the steps of:
   (a) culturing, in a liquid medium comprising a carbon source and a nitrogen source, a yeast in a logarithmic growth phase at a pH of 3.5 to 7.5 and a temperature range of 20° C. to 40° C., while aerating; and
   (b) after the yeast enters a stationary growth phase, continuing culturing the yeast in the same medium as in the step (a) at a pH that: (i) is adjusted to be equal to or higher than 7.5 and lower than 11 by addition of an alkaline substance or (ii) adjusts to be equal to or higher than 7.5 and lower than 11 when the medium of the step (a) further comprises an alkaline substance;
   wherein the yeast is *Saccharomyces cerevisiae* or *Candida utilis*, and an amount of free glutamic acid contained in the yeast is 2.3 to 10.0 wt % per dried yeast after step (b)(i) or (ii) biomass.

2. The method for culturing a yeast according to claim 1, wherein during step (b), a portion of the cultured yeast is recovered and a content of free glutamic acid in the yeast is intermittently measured.

3. The method of claim 1, further comprising a step of recovering the yeast from the liquid culture after the step (b).

4. A method for culturing a yeast, consisting essentially of the steps of:
   (a) culturing, in a liquid medium comprising a carbon source and a nitrogen source, a yeast in a logarithmic growth phase at a pH of 3.5 to 7.5 and a temperature of 20° C. to 40° C., while aerating; and
   (b) after the yeast enters a stationary growth phase, continuing culturing the yeast in the same medium as in the step (a) at a pH that: (i) is adjusted to be equal to or higher than 7.5 and lower than 11 by addition of an alkaline substance or (ii) adjusts to be equal to or higher than 7.5 and lower than 11 when the medium of the step (a) further comprises an alkaline substance;
   wherein the yeast is *Saccharomyces cerevisiae* or *Candida utilis*, and an amount of free glutamic acid contained in the yeast is 2.3 to 10.0 wt % per dried yeast after step (b)(i) or (ii) biomass.

5. The method according to claim 1, wherein the alkaline substance of step (b)(i) is ammonium hydroxide ($NH_4OH$), and the alkaline substance of step (b)(ii) is urea.

6. The method according to claim 4, wherein the alkaline substance of step (b)(i) is ammonium hydroxide ($NH_4OH$), and the alkaline substance of step (b)(ii) is urea.

* * * * *